(12) United States Patent
Streeter et al.

(10) Patent No.: US 10,405,638 B2
(45) Date of Patent: Sep. 10, 2019

(54) CONNECTED PHOTO-ACTIVATABLE FORMULATION APPLICATOR

(71) Applicant: L'Oreal, Paris (FR)

(72) Inventors: John Streeter, Redmond, WA (US); Vincenzo Casasanta, III, Woodinville, WA (US); Zane Bowman Allen Miller, Seattle, WA (US)

(73) Assignee: L'OREAL, Paris (FR)

( * ) Notice: Subject to any disclaimer, the term of this patent is extended or adjusted under 35 U.S.C. 154(b) by 6 days.

(21) Appl. No.: 15/738,089

(22) PCT Filed: Aug. 18, 2016

(86) PCT No.: PCT/US2016/047585
§ 371 (c)(1),
(2) Date: Dec. 19, 2017

(87) PCT Pub. No.: WO2017/031334
PCT Pub. Date: Feb. 23, 2017

(65) Prior Publication Data
US 2018/0168318 A1   Jun. 21, 2018

Related U.S. Application Data

(63) Continuation-in-part of application No. 14/829,370, filed on Aug. 18, 2015, now Pat. No. 10,034,530.
(Continued)

(51) Int. Cl.
*A45D 40/26* (2006.01)
*A45D 34/04* (2006.01)
*A45D 33/32* (2006.01)

(52) U.S. Cl.
CPC .......... *A45D 40/261* (2013.01); *A45D 33/32* (2013.01); *A45D 34/041* (2013.01);
(Continued)

(58) Field of Classification Search
CPC .... A45D 40/261; A45D 34/041; A45D 33/32; A45D 40/18; A45D 2200/205;
(Continued)

(56) References Cited

U.S. PATENT DOCUMENTS 8,591,133 B2 * 11/2013 Ho ....................... A45D 34/041
401/209
8,734,772 B1   5/2014 Zhou et al.
(Continued)

FOREIGN PATENT DOCUMENTS

DE   199 41 365 A1   1/2001
EP   1 218 430   3/2001
(Continued)

OTHER PUBLICATIONS

International Search Report and Written Opinion dated Oct. 27, 2016, issued in corresponding International Application No. PCT/US2016/044695, filed Jul. 29, 2016, 14 pages.
(Continued)

*Primary Examiner* — David J Walczak
(74) *Attorney, Agent, or Firm* — Christensen O'Connor Johnson Kindness PLLC

(57) ABSTRACT

An applicator device includes a photo-active formulation assembly and a photo-dose assembly operably coupled to the photo-active formulation assembly. The photo-active formulation assembly includes one or a plurality of dispenser portions and one or more photo-activatable formulation reservoirs. The photo-active formulation assembly is operable to dispense a photo-activatable formulation from the one or more photo-activatable formulation reservoirs onto one or more regions of a biological surface. The photo-dose assembly includes at least one illuminator oriented to focus electromagnetic energy onto one or more focal regions of a biological surface. The focused electro-
(Continued)

magnetic energy is of a character and for a duration sufficient to photo-activate the photo-activatable formulation dispensed from the one or more photo-activatable formulation reservoirs.

1 Claim, 11 Drawing Sheets

Related U.S. Application Data

(60) Provisional application No. 62/337,072, filed on May 16, 2016.

(52) U.S. Cl.
CPC .... *A45D 2200/205* (2013.01); *A61K 2800/81* (2013.01); *A61K 2800/874* (2013.01)

(58) Field of Classification Search
CPC .... A61N 5/06; A61K 8/8135; A61K 2800/20; A61K 2800/81; A61K 2800/874; A61K 2800/95; A61K 2800/87; A61Q 1/02; A61Q 1/06; A61Q 3/02; A61Q 19/00
See application file for complete search history.

(56) References Cited

U.S. PATENT DOCUMENTS

| | | |
|---|---|---|
| 9,456,678 B1 | 10/2016 | Harooni |
| 2003/0180690 A1 | 9/2003 | Neuberger |
| 2011/0184334 A1 | 7/2011 | Altshuler et al. |
| 2012/0024308 A1 | 2/2012 | Giron et al. |
| 2012/0109041 A1 | 5/2012 | Munz |
| 2012/0207532 A1 | 8/2012 | Ho |
| 2012/0282199 A1 | 11/2012 | Pollack et al. |
| 2013/0131575 A1 | 5/2013 | Dacey, Jr. |
| 2013/0171083 A1 | 7/2013 | Li et al. |
| 2013/0317416 A1 | 11/2013 | Samain et al. |
| 2015/0139924 A1 | 5/2015 | Zhou et al. |
| 2015/0327653 A1 | 11/2015 | Decaux et al. |
| 2017/0049212 A1 | 2/2017 | Casasanta, III |

FOREIGN PATENT DOCUMENTS

| | | |
|---|---|---|
| WO | 2009/047669 A2 | 4/2009 |
| WO | 2013/190469 A3 | 12/2013 |
| WO | 2014/091035 A1 | 6/2014 |

OTHER PUBLICATIONS

Invitation to Pay Additional Fees and, Where Applicable, Protest Fee, mailed Oct. 27, 2016, issued in corresponding International Application No. PCT/US2016/047585, filed Aug. 18, 2016, 9 pages.
International Search Report and Written Opinion dated Dec. 22 2016, issued in corresponding International Application No. PCT/US2016/047585, filed Aug. 18, 2016, 17 pages.
International Preliminary Report on Patentability with Written Opinion dated Feb. 20, 2018, for International Application No. PCT/US2016/044695, filed Jul. 29, 2016, 8 pages.
International Preliminary Report on Patentability with Written Opinion dated Feb. 20, 2018, for International Application No. PCT/US2016/047585, filed Aug. 18, 2016, 11 pages.

\* cited by examiner

US 10,405,638 B2

CONNECTED PHOTO-ACTIVATABLE FORMULATION APPLICATOR

CROSS-REFERENCE TO RELATED APPLICATIONS

This application claims the benefit of U.S. Provisional Application No. 62/337,072, filed on May 16, 2016 and of U.S. application Ser. No. 14/829,370, filed on Aug. 18, 2015, both of which are expressly incorporated herein by reference, and this application is a continuation-in-part of U.S. application Ser. No. 14/829,370.

SUMMARY

In one embodiment, an applicator device includes a photo-active formulation assembly and a photo-dose assembly operably coupled to the photo-active formulation assembly. The photo-active formulation assembly includes a dispenser portion and one or more photo-activatable formulation reservoirs. The photo-active formulation assembly is operable to dispense a photo-activatable formulation from the one or more photo-activatable formulation reservoirs onto one or more regions of a biological surface. The photo-dose assembly includes at least one illuminator oriented to focus electromagnetic energy onto one or more focal regions of a biological surface. The focused electromagnetic energy is of a character and for a duration sufficient to photo-activate the photo-activatable formulation dispensed from the one or more photo-activatable formulation reservoirs.

In one example, the photo-active formulation assembly includes at least one replaceable formulation cartridge. In another example, the photo-active formulation includes one or more photo-active polymers, photo-active oligomers, photo-active monomers, cross-linkable polymers, and the like. In another example, the photo-active formulation assembly includes one or more photo-curable materials. In another example, the photo-dose assembly includes a light ring proximate the dispenser portion.

In an embodiment, the photo-dose assembly includes at least one waveguide structure. In an embodiment, photo-dose assembly includes one or more waveguides structures configured to direct an emitted electromagnetic energy stimulus to one or more focal regions of a biological surface. Non-limiting examples of waveguide structures include electromagnetic energy waveguides, acoustic energy waveguides (e.g., ultrasonic energy waveguides), optical energy waveguides (e.g., optical fibers, photonic-crystal fibers, or the like), radiation waveguides, thermal energy waveguides, and the like. Further non-limiting examples of waveguides structures include diffractive elements (e.g., gratings, cross-gratings, or the like), diffusing elements, etchings, facets, grooves, lens structures, light-diffusing structures, mirrored structures, mirrored surfaces, optical micro-prisms, lenses (e.g., micro-lenses or the like), reflective coatings, reflective materials, reflective surfaces, texturing, thin-films, and the like, and combinations thereof. In an embodiment, the waveguide structure comprises structures suitable for directing electromagnetic energy waves.

In an embodiment, the waveguide structure comprises at least one of a transparent, translucent, or light-transmitting material, and combinations or composites thereof. Non-limiting examples of transparent, translucent, or light-transmitting materials include those materials that offer a low optical attenuation rate to the transmission or propagation of light waves. Further non-limiting examples of transparent, translucent, or light-transmitting materials include borosilicate glasses, crystals, epoxies, glasses, optically clear materials, plastics, polymers, resins, semi-clear materials, thermal resins, thermo plastics, and the like, and combinations or composites thereof.

In another example, the photo-dose assembly 26 includes a plurality of waveguide structures. In another example, the photo-active formulation assembly includes a roller assembly for dispensing the photo-activatable formulation onto the one or more regions of the biological surface and the photo-dose assembly includes a light ring proximate the roller assembly. In an embodiment, the photo-dose assembly includes one or more waveguides. In an embodiment, the roller assembly comprises one or more waveguides.

In another example, the photo-dose assembly is configured to modify a spectral parameter based on information indicative of a photo-curing composition type. For example, during operation, the photo-dose assembly includes circuitry configured to modify one more parameters associated with emission intensity, emission phase, emission polarization, emission wavelength (e.g., a peak emission wavelength, a radiation wavelength, an average emission wavelength, or the like), pulse frequency, and the like responsive to one or more inputs indicative of a photo-curing composition type.

In another example, the spectral parameter includes one or more of a wavelength of the focused electromagnetic energy, an intensity of the focused electromagnetic energy, or a duration of the focused electromagnetic energy. In another example, the photo-active formulation assembly dispenses the photo-activatable formulation from the one or more photo-activatable formulation reservoirs onto the one or more regions of a biological surface at rate commensurate with a photo-curing rate.

In another example, the at least one illuminator is arranged concentric about the dispenser portion of the photo-active formulation assembly. In another example, the electromagnetic energy is selected based on the photo-activatable formulation in the one or more photo-activatable formulation reservoirs. In another example, the focused electromagnetic energy comprises electromagnetic energy at a plurality of wavelengths, and wherein the plurality of wavelengths are operable to photo-activate a plurality of coatings of photo-activatable formulations. In another example, the photo-active formulation assembly includes at least one photo-activatable formulation nebulizer.

In another embodiment, a method of applying a photo-activatable formulation includes dispensing, by a dispenser portion of a photo-active formulation assembly, photo-activatable formulation from one or more photo-activatable formulation reservoirs onto one or more regions of a biological surface and focusing, by a photo-dose assembly operably coupled to the photo-active formulation assembly, electromagnetic energy from at least one illuminator onto one or more focal regions of the biological surface. The focused electromagnetic energy is of a character and for a duration sufficient to photo-activate the photo-activatable formulation dispensed from the one or more photo-activatable formulation reservoirs.

In one example, the photo-active formulation assembly is a part of a replaceable formulation cartridge, and wherein dispensing the photo-activatable formulation includes dispensing the photo-activatable formulation from the replaceable formulation cartridge. In another example, the method further includes removing the replaceable formulation cartridge from an applicator that includes the photo-dose assembly, coupling a second replaceable formulation cartridge to the applicator, and dispensing, from the second replaceable formulation cartridge, a second photo-activatable formulation onto the one or more regions of the biological surface. In another example, the method further includes focusing, by the photo-dose assembly, electromagnetic energy from the at least one illuminator onto the one or more focal regions of the biological surface, the focused electromagnetic energy of a character and for a duration sufficient to photo-activate the second photo-activatable formulation dispensed from the second replaceable formulation cartridge.

In an embodiment, an applicator device includes a photo-active formulation assembly including one or a plurality of dispenser portions and one or more photo-activatable formulation reservoirs, the photo-active formulation assembly being operable to dispense a photo-activatable formulation from the one or more photo-activatable formulation reservoirs onto one or more regions of a biological surface; and a photo-dose assembly operably coupled to the photo-active formulation assembly, the photo-dose assembly including at least one illuminator oriented to focus electromagnetic energy onto one or more focal regions of a biological surface, the focused electromagnetic energy of a character and for a duration sufficient to photo-activate the photo-activatable formulation dispensed from the one or more photo-activatable formulation reservoirs.

In an embodiment, the applicator device includes at least one proximity sensor configured to activate the at least one illuminator. In an example, the at least one proximity sensor is selected from the group consisting of infrared, acoustic, ultrasound, conductance, dielectric, capacitance, electrochemical, fluorescence, force, heat, thermocouple, thermistor, interdigital, optical, physiological, and inductive sensors. In an example, the proximity sensor requires contact to the biological surface to activate the at least one illuminator.

In an embodiment, the illuminator is operable to project images onto the biological surface. In an example, images include one or more of instructions for a treatment, a target or guide display to direct treatment, or a notification.

In an embodiment, the applicator device includes a camera operable to take images of the biological surface.

In an embodiment, the dispenser portion comprises a biocompatible conductive coating on an exterior of the dispenser portion.

In an embodiment, the dispenser portion includes a ball operable to roll on the biological surface. In an example, the biocompatible conductive coating includes polyethylenedioxythiophene, nano-composites thereof, or grapheme. In an example, the biocompatible conductive coating is an electrode.

In an embodiment, the applicator device includes a shield proximate of the dispenser portion, wherein the shield comprises a one-way mirror operable to allow transmission of light from the at least one illuminator towards the dispenser portion. In an example, the shield is operable to block reflected light. In an example, the shield has a hemispherical shape.

In an embodiment, the photo-active formulation assembly includes a machine readable feature encoded with information. In an example, the machine readable feature is a radio frequency identification tag, a magnetic chip, a barcode, a 2-D barcode, or any electronically readable chip. In an example, the information includes the wavelength, time, amplitude, or a combination thereof, for activating the photo-active formulation.

In an embodiment, the photo-dose assembly includes a reader configured to lie in proximity to the machine readable feature, and the reader can read the information provided on the machine readable feature. In an example, the photo-dose assembly is operable to control the wavelength of the electromagnetic energy delivered by the illuminator, the time the illuminator is on, the amplitude of the electromagnetic energy produced by the illuminator, or any combination, based on the information on the machine readable feature.

In an embodiment, the photo-active formulation assembly includes a machine readable feature encoded with the wavelength, time, or amplitude at which the photo-active formulation is activated, and the photo-dose assembly includes a reader in proximity to the machine readable feature.

In an embodiment, the photo-active formulation assembly includes one or more waveguides fixed to an exterior surface.

In an embodiment, the applicator device includes a cavity between an interior of the photo-dose assembly and an exterior of the photo-active formulation assembly, wherein the interior of the photo-dose assembly and the exterior of the photo-active formulation assembly have a reflective surface. In an example, the cavity forms an elliptical reflector.

In an embodiment, the dispenser portion comprises a ball having a flexible outer surface and a fluid or gel inside the flexible outer surface.

In an embodiment, an applicator device includes a photo-active formulation assembly including one or a plurality of dispenser portions and one or more photo-activatable formulation reservoirs, the photo-active formulation assembly being operable to dispense a photo-activatable formulation from the one or more photo-activatable formulation reservoirs onto one or more regions of a biological surface; and a photo-dose assembly configured to be operably coupled to the photo-active formulation assembly, wherein the photo-active formulation assembly allows insertion into the photo-does assembly in a single orientation, the photo-dose assembly including at least one illuminator oriented to focus electromagnetic energy onto one or more focal regions of a biological surface, the focused electromagnetic energy of a character and for a duration sufficient to photo-activate the photo-activatable formulation dispensed from the one or more photo-activatable formulation reservoirs.

In an embodiment, a method of applying a photo-activatable formulation includes dispensing, by a dispenser portion of a photo-active formulation assembly, photo-activatable formulation from one or more photo-activatable formulation reservoirs onto one or more regions of a biological surface; reading from a machine readable feature on the photo-active formulation assembly, information for activating the photo-activatable formulation; and focusing, by a photo-dose assembly operably coupled to the photo-active formulation assembly, electromagnetic energy from at least one illuminator onto one or more focal regions of the biological surface, wherein the wavelength of the electromagnetic energy, the time the illuminator is on, the amplitude of the electromagnetic energy, or any combination, is based on the information read from the machine readable feature.

This summary is provided to introduce a selection of concepts in a simplified form that are further described below in the Detailed Description. This summary is not intended to identify key features of the claimed subject matter, nor is it intended to be used as an aid in determining the scope of the claimed subject matter.

DESCRIPTION OF THE DRAWINGS

The foregoing aspects and many of the attendant advantages of this invention will become more readily appreciated as the same become better understood by reference to the following detailed description, when taken in conjunction with the accompanying drawings, wherein.

DETAILED DESCRIPTION

Figure 1:
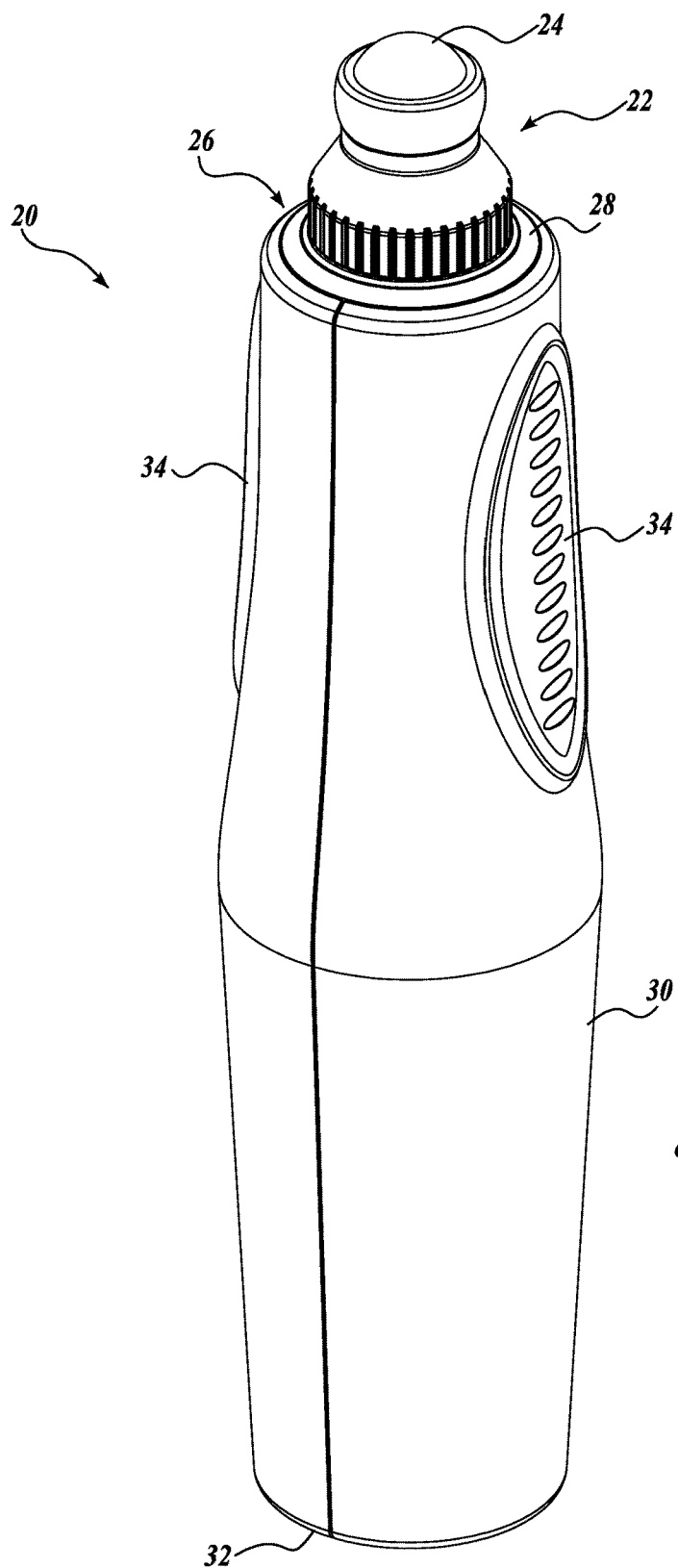
FIG. 1 depicts a perspective view of an embodiment of an applicator for dispensing photo-activatable formulations and photo-activating the dispensed photo-activatable formulations, in accordance with embodiments described herein.

Formulation applicators are used to apply formulations to skin and other biological surfaces. The ability to apply a formulation from an applicator can be especially convenient for users. Other formulation containers, such as jars, bottles, and the like, lead to waste amounts of formulation in the containers and reduced usable life of formulation from exposure to air and other environmental factors. Formulations applied to skin include makeup, personal soaps, skin care products, hair care products or any other cosmetic products.

Some formulations have been developed to be activated by light or other electromagnetic energy. These formulations, sometimes called photo-activatable formulations, are photo-activatable in some manner by exposure to electromagnetic energy of a particular character and for a particular duration. In some examples, activation of the photo-activatable formulations includes material changes of the photo-activatable formulations, reactions of the photo-activatable formulations, or any other type of action or change by the photo-activatable formulations. In an embodiment, material changes of the photo-activatable formulations include changes in viscosity responsive to an electromagnetic energy stimulus. In some examples, a material change or reaction includes cross-linking, controlled release, or radical generation. When the photo-activatable formulations are exposed to electromagnetic energy at the activation wavelength, the electromagnetic energy activates the photo-activatable formulations, causing the change or action. In some examples, the activation wavelength is a specific wavelength or a range of wavelengths. In other examples, the photo-active formulation includes at least one of photo-active polymers, photo-active oligomers, photo-active monomers, cross-linkable polymers, or photo-curable materials.

Some examples of photo-activatable formulations include cross-linked polymers and oligomers for foundation, lipstick, nail polish, dermal covers, dermal fillers, and other cosmetic formulations. Several examples of cross-linked polymers and oligomers include photo-radical initiated polyethylene glycol acrylates and photo-crosslinkable stilbazole (SbQ) functionalized backbones (SMA-SbQ, PVA-SbQ). In one example, some PVA-SbQ materials are efficiently crosslinked using ultraviolet electromagnetic energy at a wavelength of 365 nm. Other formulations are being developed that are designed to crosslink at longer wavelengths into the visible portion of the spectrum (i.e., with wavelengths greater than 400 nm).

Examples of photo-activatable formulations are described in greater detail in U.S. Patent Application Publication No. 2013/0171083, entitled "Photo-Curable Cosmetic Compositions"; U.S. Patent Application Publication No. 2015/0139924, entitled "Fast Curing Cosmetic Compositions for Tack Free Surface Photocuring of Radically Polymerizable Resins with UV-LED"; U.S. Pat. No. 8,734,772, entitled "Photo-Curable Resin for Cosmetic Application"; and International Publication No. WO 2013/190469, entitled "Cosmetic Process for Making Up and/or Caring for the Lips," the contents of each of which are incorporated herein by reference.

Figure 2:
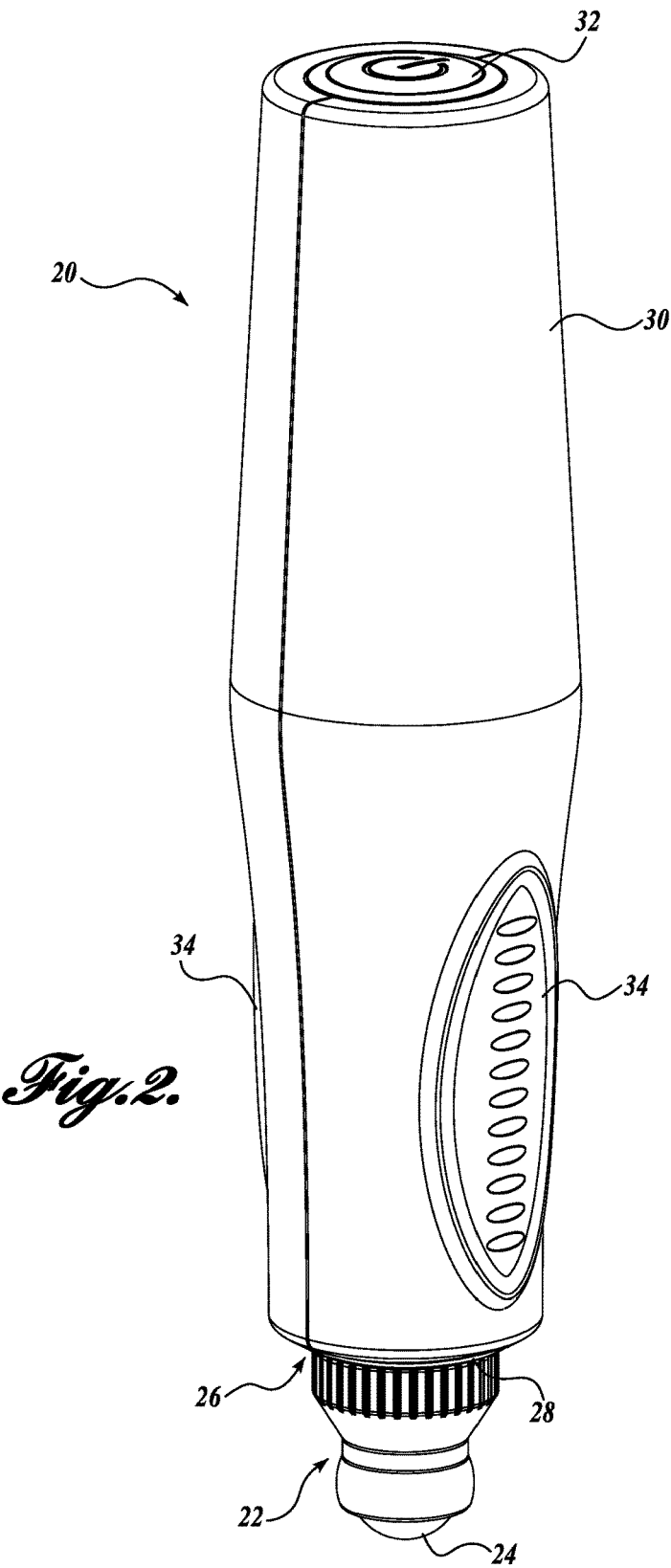
FIG. 2 depicts another perspective view of the embodiment of the applicator depicted in FIG. 1, in accordance with embodiments described herein.
Figure 3:
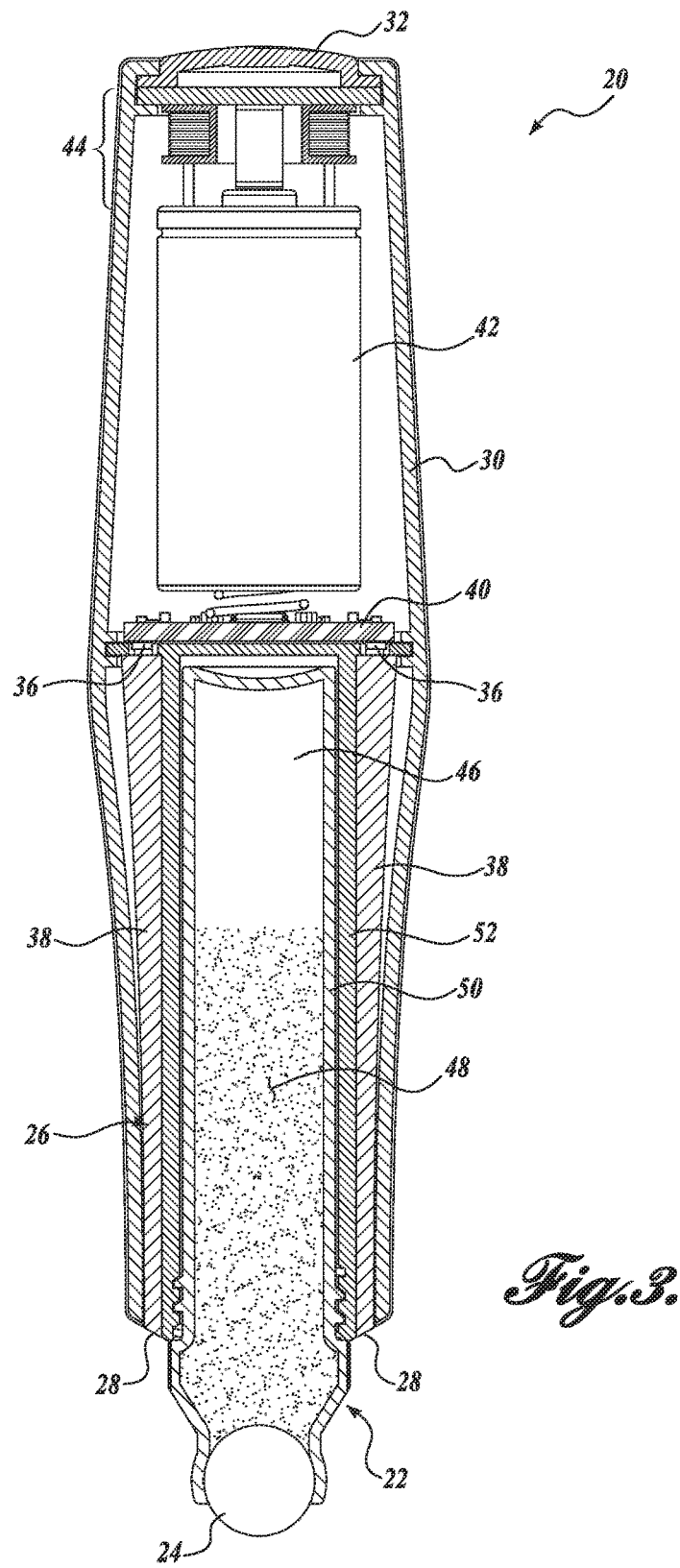
FIG. 3 depicts a side cross-sectional view of the embodiment of the applicator depicted in FIG. 1, in accordance with embodiments described herein.
Figure 4:
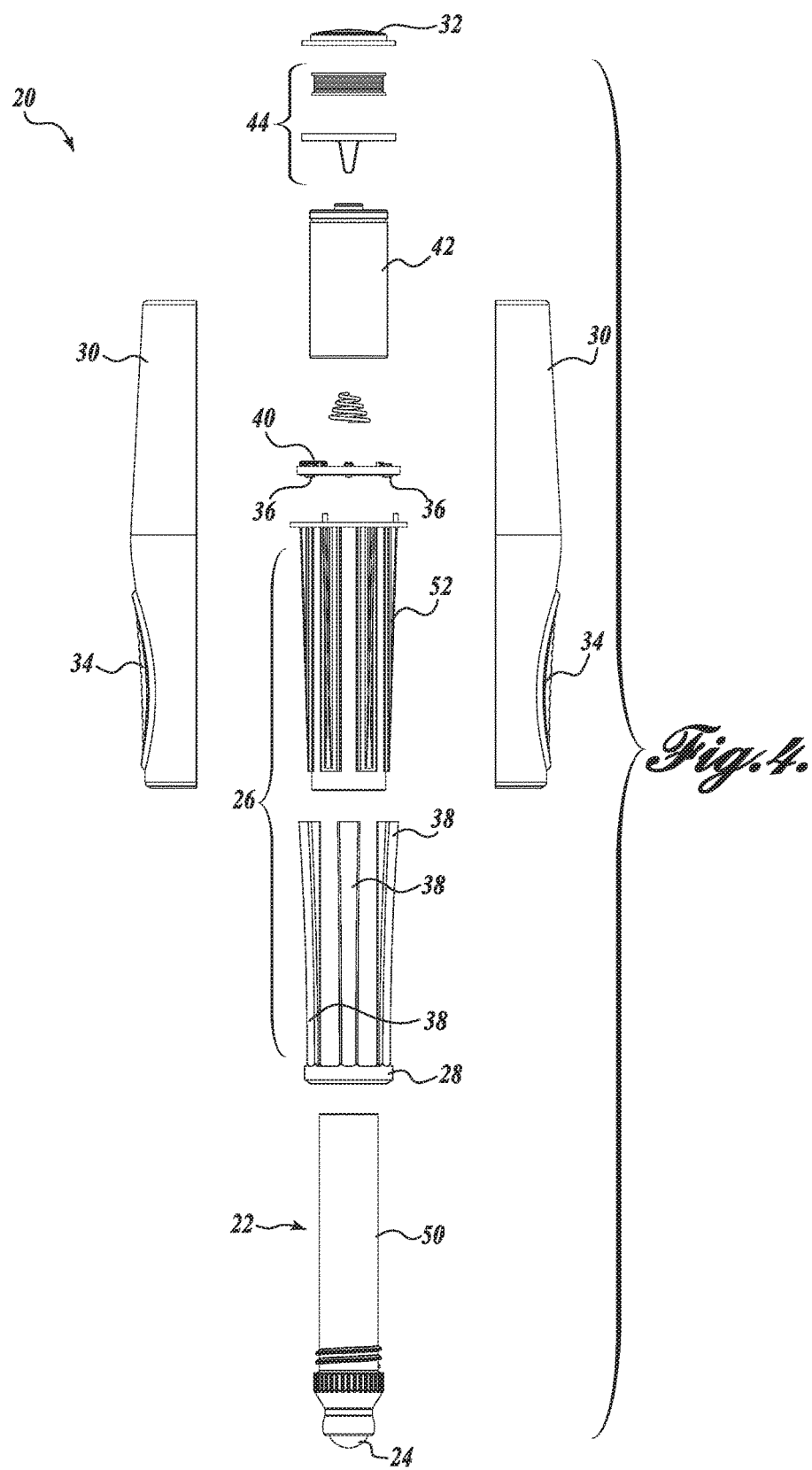
FIG. 4 and FIG. 5 depict side and perspective exploded views, respectively, of the embodiment of the applicator depicted in FIG. 1, in accordance with embodiments described herein.
Figure 5:
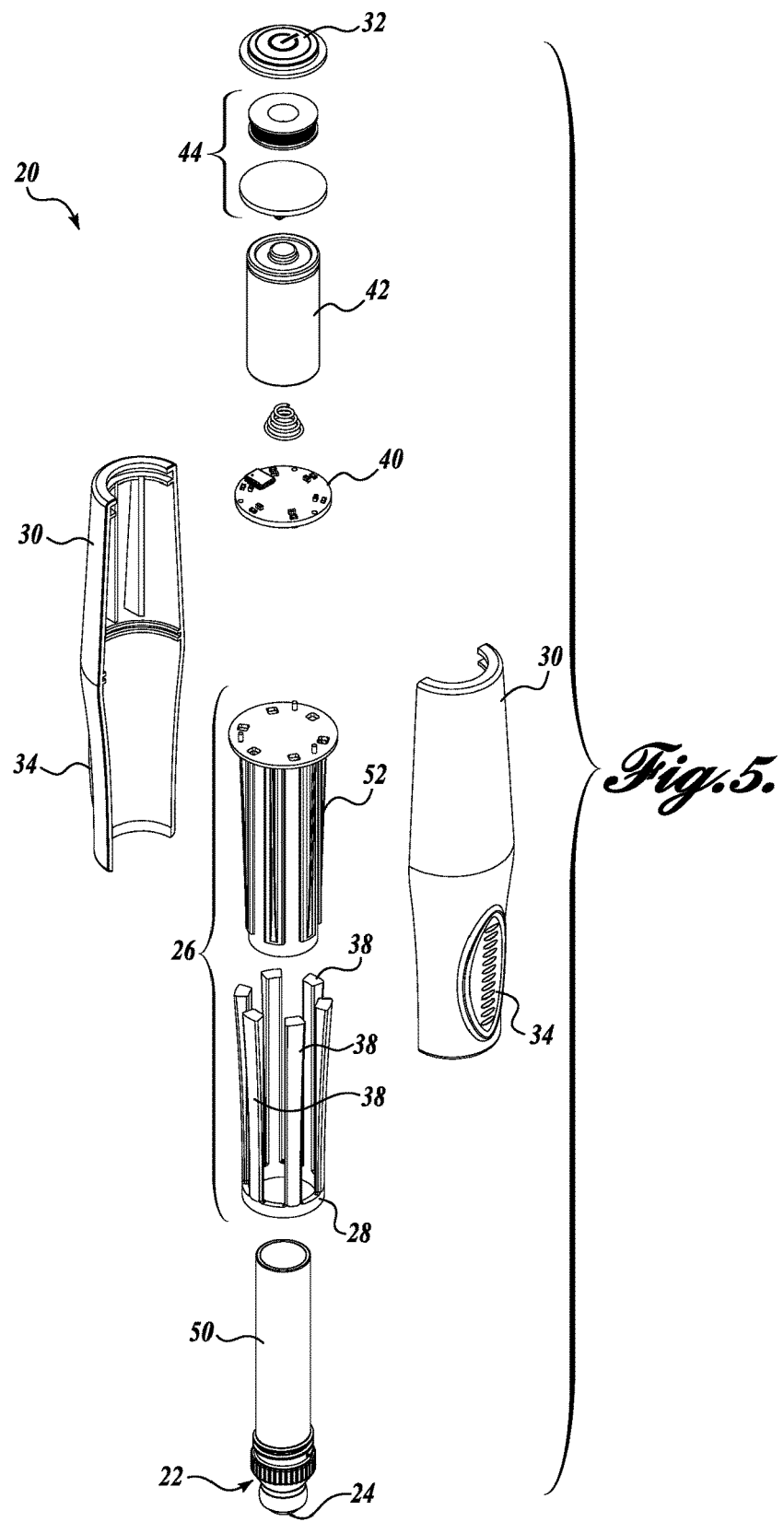
Figure 6:
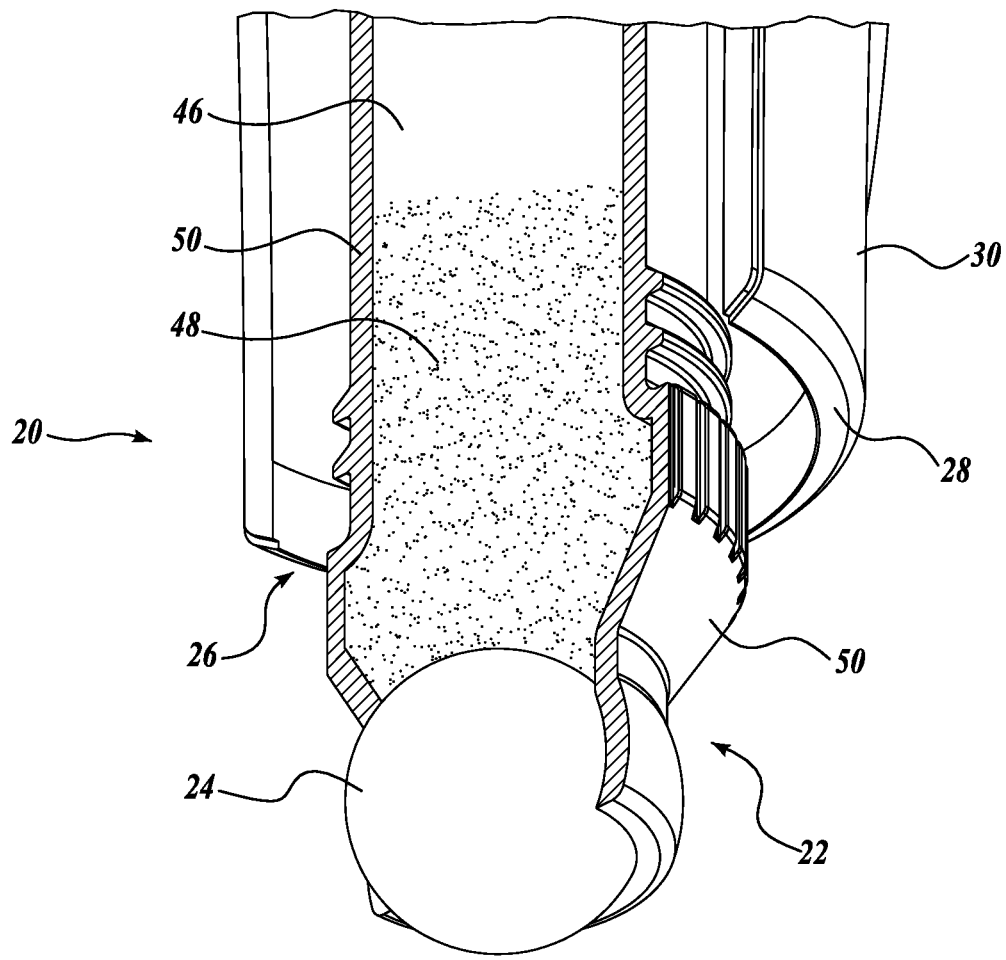
FIG. 6 depicts a partial cross-sectional view of an embodiment of a dispenser end of the applicator depicted in FIG. 1, in accordance with embodiments described herein.
Figure 7:
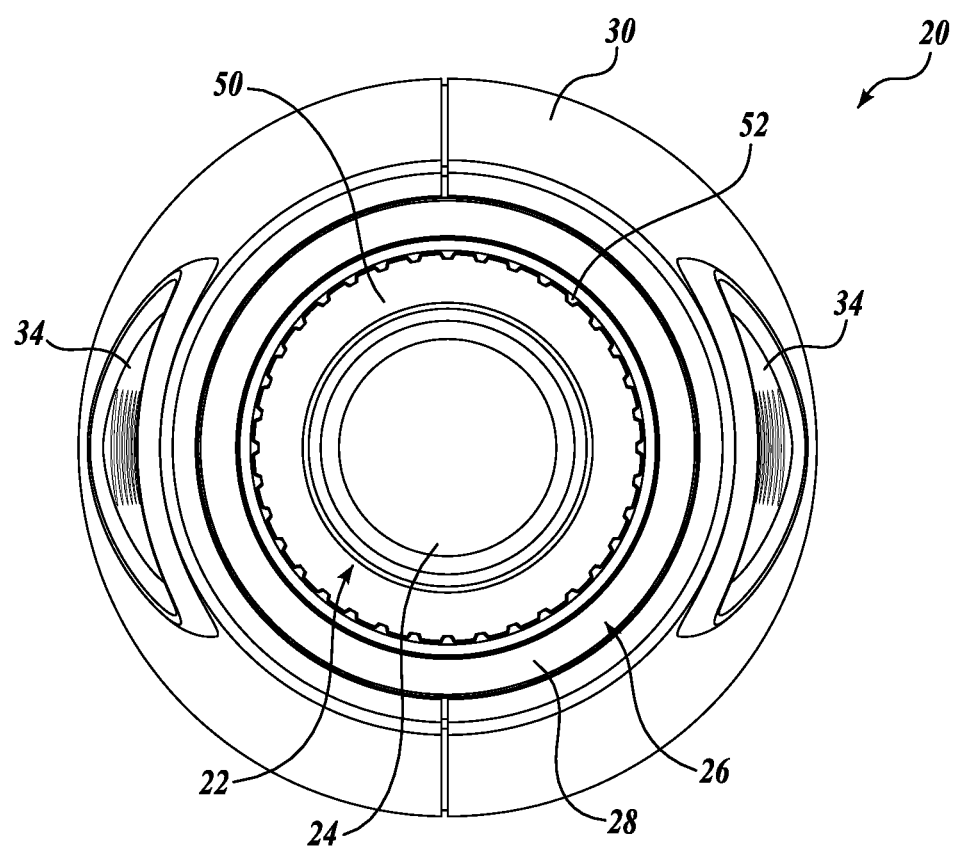
FIG. 7 depicts an end view of an embodiment of a dispenser end of the embodiment of the applicator depicted in FIG. 1, in accordance with embodiments described herein.
Figure 8:
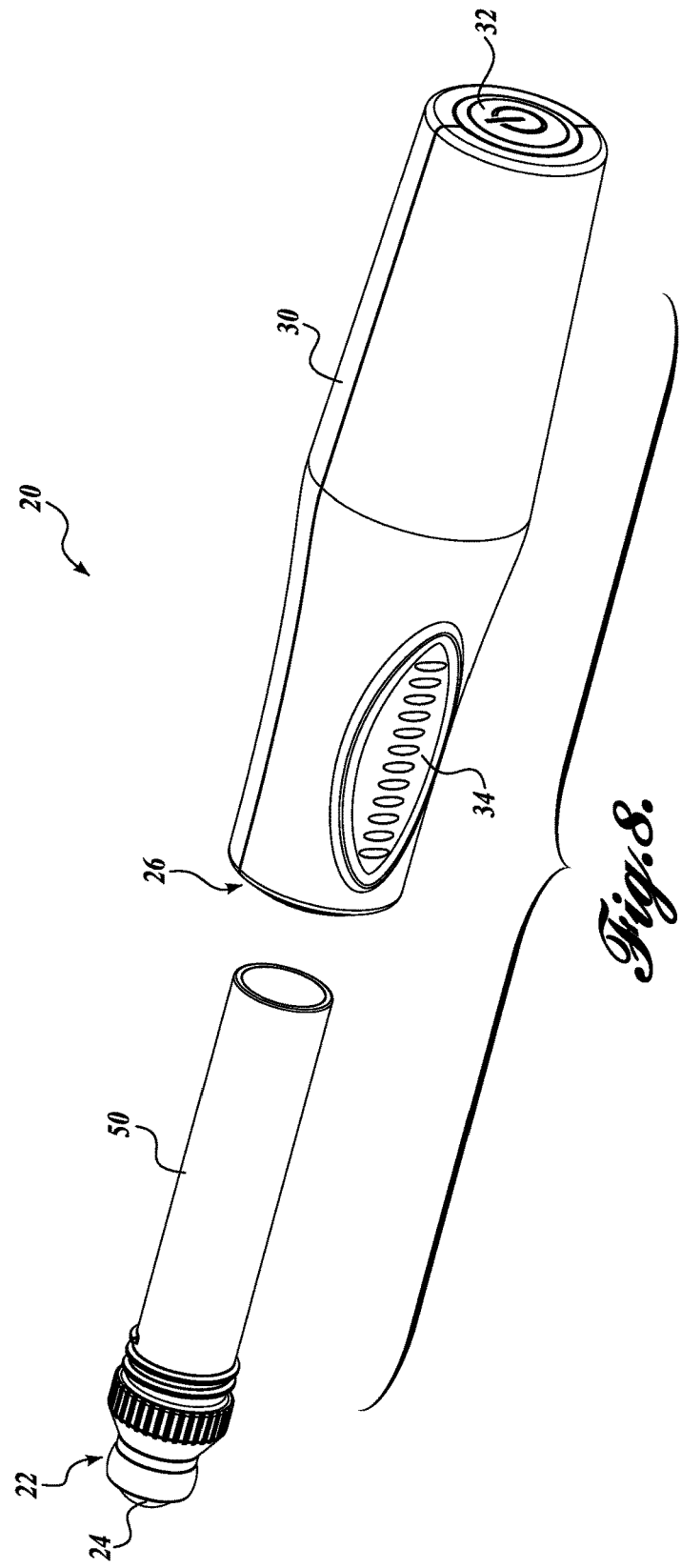
FIG. 8 depicts a perspective view of the embodiment of the applicator depicted in FIG. 1, in accordance with embodiments described herein.

Depicted in FIGS. 1 to 8 are embodiments of an applicator 20 for dispensing photo-activatable formulations and activating the dispensed photo-activatable formulations. FIGS. 1 and 2 depict perspective views of embodiments of the applicator 20. FIG. 3 depicts a side cross-sectional view of embodiments of the applicator 20. FIGS. 4 and 5 depict side and perspective exploded views, respectively, of embodiments of the applicator 20. FIG. 6 depicts a partial cross-sectional view of an embodiment of a dispenser end of the applicator 20. FIG. 7 depicts an end view of an embodiment of a dispenser end of the applicator 20. FIG. 8 depicts a perspective view of an embodiment of the applicator 20.

As depicted in FIGS. 1 and 2, the applicator 20 includes a photo-active formulation assembly 22. The photo-active formulation assembly 22 includes a dispenser portion 24 operable to dispense a photo-activatable formulation onto one or more regions of a biological surface (e.g., a portion of skin). In the particular embodiment shown in FIGS. 1 and 2, the dispenser portion 24 is a ball dispenser. In some examples, the ball of the ball dispenser is a metal ball, a ceramic ball, or a polymer ball. In some embodiments, the dispenser portion 24 comprises a dispenser having a regular or irregular cross-sectional geometry. In some embodiments, the dispenser portion 24 comprises a dispenser having a spheroid geometric shape, a cylindrical shape, and the like. In some embodiments, the dispenser portion 24 comprises a textured surface. In some embodiments, the dispenser portion 24 comprises a surface having at least one hydrophobic coating, hydrophilic coating, and the like. In some embodiments, the dispenser portion 24 comprises a surface material having a coefficients of friction ranging from about 0.15 to about 0.3. In some embodiments, the dispenser portion 24 comprises a surface material having a coefficients of friction ranging from about 0.005 to 0.2.

In some embodiments, as discussed in greater detail below, the applicator 20 includes one or more photo-activatable formulation reservoirs from which the photo-activatable formulation is dispensed onto one or more regions of a biological surface.

The applicator 20 also includes a photo-dose assembly 26 operably coupled to the photo-active formulation assembly 22. As discussed in greater detail below, the photo-dose assembly 26 includes at least one illuminator oriented to focus electromagnetic energy onto one or more focal regions of a biological surface. The focused electromagnetic energy from the photo-dose assembly 26 is of a character and for a duration sufficient to photo-activate the photo-activatable formulation dispensed from the photo-active formulation assembly 22.

In the embodiment shown in FIGS. 1 and 2, the photo-dose assembly 26 includes a light ring 28 located substantially concentric with the photo-active formulation assembly 22. The light ring 28 is also located such that electromagnetic energy emitted from at least one illuminator of the photo-dose assembly 26 passes through the light ring 28 and is directed toward one or more focal regions of a biological surface. In one embodiment, a spectral parameter type (e.g., a wavelength, an intensity, or a duration) of the electromagnetic energy emitted by the photo-dose assembly 26 is selected based on information indicative of a photo-curing composition type. In some embodiments, the light ring 28 is configured to focus the electromagnetic energy emitted by the at least one illuminator and includes one or more of a lens, a diffuser, or a grating.

The applicator 20 also includes a housing 30. In one example, the housing 30 holds the photo-active formulation assembly 22 and the photo-dose assembly 26 such that at least one illuminator of the photo-dose assembly 26 is oriented to focus electromagnetic energy onto one or more focal regions of a biological surface with the focused electromagnetic energy of a character and for a duration sufficient to photo-activate the photo-activatable formulation dispensed from one or more photo-activatable formulation reservoirs of the photo-active formulation assembly 22. In some embodiments, the applicator 20 also includes features, such as an activator such as a button 32 or grips 34, to aid in use of the applicator 20 by a user. For example, in one embodiment, the button 32 is power button on an end opposite the photo-active formulation assembly 22 and configured to toggle power to the photo-dose assembly 26. In another embodiment, the housing 30 also includes grips 34 that add to the convenience for a user to grip the applicator 20.

As can be seen in FIGS. 3 to 5, the photo-dose assembly 26 of the applicator 20 includes at least one illuminator 36. Non-limiting examples of illuminators 36 include arc flashlamps, cavity resonators, continuous wave bulbs, electric circuits, electrical conductors, electromagnetic energy emitting emitters, electromagnetic radiation emitters, electro-mechanical components, electro-opto components, incandescent emitters, laser diodes, lasers, light-emitting diodes (e.g., organic light-emitting diodes, polymer light-emitting diodes, polymer phosphorescent light-emitting diodes, microcavity light-emitting diodes, high-efficiency light-emitting diodes, and the like), quantum dots, and the like.

In one example, the at least one illuminator 36 is a source of electromagnetic energy, such as a light emitting diode (LED). In the depicted example, the at least one illuminator 36 includes six LEDs; however, the at least one illuminator 36 may include any number of illuminators, such as a single illuminator or a plurality of illuminators. The at least one illuminator 36 is arranged to focus electromagnetic energy onto one or more focal regions of a biological surface of a character and for a duration sufficient to photo-activate the photo-activatable formulation dispensed from one or more photo-activatable formulation reservoirs of the photo-active formulation assembly 22. In one example, the at least one illuminator 36 includes a patterned illuminator having a plurality of spaced-apart electromagnetic energy emitting elements.

In one embodiment, one or more spectral parameters of the electromagnetic energy emitted by the at least one illuminator 36 (e.g., a wavelength of the electromagnetic energy, an intensity of the electromagnetic energy, a duration of the electromagnetic energy, and the like) are selected based on a particular photo-activatable formulation. In one embodiment, the at least one illuminator 36 includes at least one LED that includes III-V semiconductor materials or III-N semiconductor materials. With III-V and III-N LED technology, wavelengths are available from the ultraviolet range (i.e., from about 10 nm to about 400 nm), through the visible range (i.e., from about 400 nm to about 700 nm), and into the infrared range (from about 700 nm to about 1 mm) of the electromagnetic spectrum. The power density and dimensions of these devices also cover a wide range.

In an embodiment, a plurality of illuminators are configured to emit radiation having one or more peak emission wavelengths in the infrared, visible, or ultraviolet spectrum, or combinations thereof. For example, during operation, at least illuminator 36 comprises a peak emission wavelength ranging from about 700 nanometers to about 1 millimeter. In an embodiment, at least one illuminator 36 comprises a peak emission wavelength ranging from about 5 micrometers to about 10 micrometers. In an embodiment, at least on illuminator 36 comprises a peak emission wavelength ranging from about 400 nanometers to about 700 nanometers.

In an embodiment, the photo-dose assembly 26 includes circuitry configured to vary one or more of emission intensity, emission phase, emission polarization, emission wavelength (e.g., a peak emission wavelength, a radiation wavelength, an average emission wavelength, or the like), pulse frequency, and the like.

In the particular embodiment shown in FIGS. 3 to 5, the photo-dose assembly 26 also includes at least one waveguide structure 38. In the depicted embodiment, the at least one illuminator 36 is arranged to emit electromagnetic energy toward the at least one waveguide structure 38. The at least one waveguide structure 38 is configured to transmit the electromagnetic energy from the at least one illuminator 36.

In the particular embodiment shown in FIGS. 3 to 5, the at least one waveguide structure 38 includes six electromagnetic energy pipes. In some examples, the at least one waveguide structure 38 is formed from segmented glass, polymer, or any other material that can transmit electromagnetic energy. In one embodiment, the number of at least one waveguide structure 38 is equal to a number of the at least one illuminator 36; however, differing numbers of the at least one illuminator 36 and the at least one waveguide structure 38 are possible. In one embodiment, the numbers of the at least one illuminator 36 and the at least one waveguide structure 38 are selected based on based on a size of the applicator 20, light flux requirements of photo-activatable formulations, or any other factor.

In the depicted embodiment, the source of electromagnetic energy also includes the light ring 28. The at least one waveguide structure 38 are configured to transmit the electromagnetic energy from the at least one illuminator 36 to the light ring 28. One or both of the at least one waveguide structure 38 or the light ring 28 is configured to focus the electromagnetic energy and the photo-dose assembly 26 is oriented to direct the focused electromagnetic energy to one or more focal regions of a biological surface to photo-activate photo-activatable formulation dispensed from the one or more photo-activatable formulation reservoirs.

In some embodiments, the applicator 20 also includes a controller 40, such as control circuitry, for the at least one illuminator 36. In one example, the controller 40 controls power to the at least one illuminator 36. In another example, the controller 40 modifies a spectral parameter of the electromagnetic energy emitted from the at least one illuminator 36 (e.g., wavelength, intensity, duration, and the like) based on information indicative of a photo-curing composition type, photo-curing protocol, and the like. In another example, the controller 40 modifies a parameter associated with an illumination temporal pattern, an illumination spaced-apart pattern, and the like based on information indicative of a photo-curing protocol.

In some examples, the controller 40 modifies a spectral parameter of the electromagnetic energy emitted from the at least one illuminator 36 such that the emitted electromagnetic energy is configured to photo-activate the dispensed photo-activatable formulation on the one or more regions of a biological surface.

In some embodiments, the applicator 20 also includes a power source 42, such as a rechargeable battery. In an embodiment, the applicator 20 includes one or more power sources 42. Non-limiting examples of power sources include one or more button cells, chemical battery cells, a fuel cell, secondary cells, lithium ion cells, micro-electric patches, nickel metal hydride cells, silver-zinc cells, capacitors, super-capacitors, thin film secondary cells, ultra-capacitors, zinc-air cells, or the like. Further non-limiting examples of power sources include one or more generators (e.g., electrical generators, thermo energy-to-electrical energy generators, mechanical-energy-to-electrical energy generators, micro-generators, nano-generators, or the like) such as, for example, thermoelectric generators, piezoelectric generators, electromechanical generators, or the like. In an embodiment, the power source includes at least one rechargeable power source. In an embodiment, the power source includes one or more micro-batteries, printed micro-batteries, thin film batteries, fuel cells (e.g., biofuel cells, chemical fuel cells, etc.), and the like.

The power source 42 is configured to provide power to the at least one illuminator 36. In one embodiment, the applicator includes a power controller 44. In some examples, the power controller 44 includes one or more of a charging coil, a charging circuit, or an actuator for the power button 32. In the embodiment where the power controller 44 includes a charging coil, the charging coil permits the power source 42 to be recharged inductively. In one example, the applicator 20 is recharged when placed in a cradle configured to inductively recharge the power source 42 of the applicator 20.

In some embodiments, the applicator 20 also includes one or more photo-activatable formulation reservoirs 46 that hold photo-activatable formulation 48. The photo-active formulation assembly 22 is arranged to dispense the photo-activatable formulation 48 to a one or more regions of a biological surface. For example, in the depicted embodiment, the photo-active formulation assembly 22 is a roller assembly for dispensing the photo-activatable formulation onto the one or more regions of a biological surface. As the roller assembly is rolled over one or more regions of a biological surface, an amount of the photo-activatable formulation 48 is dispensed to the one or more regions of a biological surface. In one embodiment, the roller assembly is a waveguide that guides electromagnetic energy from the photo-dose assembly 26. In another embodiment, photo-active formulation assembly 22 dispenses the photo-activatable formulation 48 from the one or more photo-activatable formulation reservoirs 46 onto one or more regions of a biological surface at rate commensurate with a photo-curing rate of the photo-activatable formulation 48. In another embodiment, the photo-active formulation assembly 22 includes at least one photo-activatable formulation nebulizer. In one example, the photo-activatable formulation nebulizer delivers the photo-activatable formulation 48 in the form of a mist when the photo-active formulation assembly 22 dispenses the photo-activatable formulation 48.

In one embodiment, the one or more photo-activatable formulation reservoirs 46 are configured to limit exposure of the photo-activatable formulation 48 to electromagnetic energy prior to the photo-activatable formulation 48 being dispensed to the one or more regions of a biological surface. Limiting exposure of the photo-activatable formulation 48 to electromagnetic energy prior to being dispensed reduces the possibility that the photo-activatable formulation 48 will be activated before it is dispensed. In one embodiment, the one or more photo-activatable formulation reservoirs 46 are formed integrally with the applicator 20. In another embodiment, as discussed below, the one or more photo-activatable formulation reservoirs 46 are removable from the applicator 20.

In the embodiments depicted in FIGS. 3 to 6 and FIG. 8, the photo-active formulation assembly 22, including the one or more photo-activatable formulation reservoirs 46 and the photo-activatable formulation 48, are contained within a replaceable formulation cartridge 50. In one embodiment, the replaceable formulation cartridge 50 is removably couplable to the applicator 20. In the example where the at least one illuminator 36 is fixed in the applicator 20, the photo-active formulation assembly 22 is also removably couplable to the photo-dose assembly 26. In the depicted embodiment, the replaceable formulation cartridge 50 includes external threads that engage internal threads of a structural member 52 of the applicator 20. In other embodiments, the replaceable formulation cartridge 50 is removably couplable to the applicator 20 by other mechanisms, such as a snap connector, a magnetic coupling, or any other releasable coupling mechanism.

This interchangeability of formulation cartridges allows a user to couple the replaceable formulation cartridge 50 to the source of electromagnetic energy, dispense the photo-activatable formulation 48 from the replaceable formulation cartridge 50 to a one or more regions of a biological surface, and focus electromagnetic energy onto one or more focal regions of a biological surface (e.g., by the at least one illuminator 36) to activate the photo-activatable formulation 48 dispensed on the one or more regions of the biological surface. The replaceable formulation cartridge 50 can then be removed from the applicator 20 and then a different formulation cartridge can be coupled to the applicator 20. This interchangeability of formulation cartridges allows different photo-active assemblies to be used with the photo-dosing assembly 26. In practice, a user is able to dispense different photo-activatable formulations from different formulation cartridges and activate the different photo-activatable formulations using the same photo-dosing assembly 26 of the applicator 20. It also allows the formulation cartridges to be disposable items while the other portions of the applicator 20 are used over a longer period of time. In one embodiment, focused electromagnetic energy from the photo-dose assembly 26 comprises electromagnetic energy at multiple wavelengths where the multiple wavelengths are operable to photo-activate multiple coatings of photo-activatable formulations.

In the embodiment depicted in FIGS. 3 to 5, the at least one illuminator 36 is located at an end of the replaceable formulation cartridge 50 opposite the dispenser portion 24. This positioning places the at least one illuminator 36 away from the area where the replaceable formulation cartridge 50 is inserted into and coupled to the applicator 20 so that the at least one illuminator 36 is not damaged or misaligned by the coupling or decoupling of the replaceable formulation cartridge 50. This positioning also places the at least one illuminator 36 closer to the power source 42. While the at least one illuminator 36 is located at an end of the replaceable formulation cartridge 50 opposite the photo-active formulation assembly 22, the at least one waveguide structure 38 and the light ring 28 are arranged to transmit the electromagnetic energy from the at least one illuminator 36 and emit the focused electromagnetic energy toward the one or more regions of a biological surface where the photo-activatable formulation 48 has been dispensed.

In one embodiment, where the replaceable formulation cartridge 50 is removably couplable to the applicator 20, the replaceable formulation cartridge 50 includes an identifier. In some examples, the identifier identifies one or more of the replaceable formulation cartridge 50, the photo-activatable formulation 48 inside the replaceable formulation cartridge 50, an activation wavelength of the photo-activatable formulation 48 inside the replaceable formulation cartridge 50, an activation power of the photo-activatable formulation 48 inside the replaceable formulation cartridge 50, or any other information about the photo-activatable formulation 48 or the replaceable formulation cartridge 50. In some examples, the identifier has the form of one or more of a radio-frequency identification (RFID) tag, a color on the replaceable formulation cartridge 50, a barcode on the replaceable formulation cartridge 50, printed information on the replaceable formulation cartridge 50, or any other kind of identifier.

In some embodiments, one or more spectral parameters of the source of electromagnetic energy are variable. In one example, the at least one illuminator 36 includes a plurality of illuminators having different wavelengths that can be powered separately. In another example, the at least one illuminator 36 is capable of being powered at different levels of power. In yet another example, the controller 40 controls the one or more spectral parameters of the at least one illuminator 36. In one embodiment, where the characteristics of the source of electromagnetic energy are variable and the replaceable formulation cartridge 50 includes an identifier, one or more spectral parameters of the source of electromagnetic energy are modified based on the identifier of the replaceable formulation cartridge 50. For example, the identifier may indicate that the photo-activatable formulation 48 has an activation wavelength of 365 nm and the source of electromagnetic energy is adjusted to emit electromagnetic energy at about 365 nm when the replaceable formulation cartridge 50 is coupled to the applicator 20.

In the end view of the applicator 20 depicted in FIG. 7, the dispenser portion 24 of the photo-active formulation assembly 22 is shown as being located substantially concentrically with the light ring 28. In this arrangement, the electromagnetic energy emitted from the light ring 28 surrounds the area of the photo-active formulation assembly 22. This increases the likelihood that any photo-activatable formulation dispensed by the photo-active formulation assembly 22 will be exposed to focused electromagnetic energy emitted from the light ring 28. The proximity of the light ring 28 to the photo-active formulation assembly 22 also decreases the time between the dispensing of the photo-activatable formulation by the photo-active formulation assembly 22 and the exposure of the dispensed photo-activatable formulation to the focused electromagnetic energy emitted by the light ring 28.

The benefits of the embodiments of the applicator 20 described herein include that the photo-activatable formulation is dispensed from and activated by a single, self-contained unit. Conventional formulation applicators dispense formulations but do not include sources of electromagnetic energy. Thus, even if a conventional formulation applicator was used to dispense a photo-activatable formulation, a separate light device would be required to expose the photo-activatable formulation to the appropriate electromagnetic energy. The two-step process of applying the photo-activatable formulation with an applicator and activating the photo-activatable formulation with a separate light source is cumbersome for the user and risks improper application and/or activation of the photo-activatable formulation. In contrast to the issues with conventional formulation applicators, the embodiments of the applicator 20 described herein limit exposure of the photo-activatable formulation to electromagnetic energy before the photo-activatable formulation is dispensed, reduce the time period between applying the photo-activatable formulation to the one or more regions of a biological surface and activating the photo-activatable formulation using electromagnetic energy, and emit activating electromagnetic energy in close proximity to the location where the photo-activatable formulation is dispensed.

Figure 9:
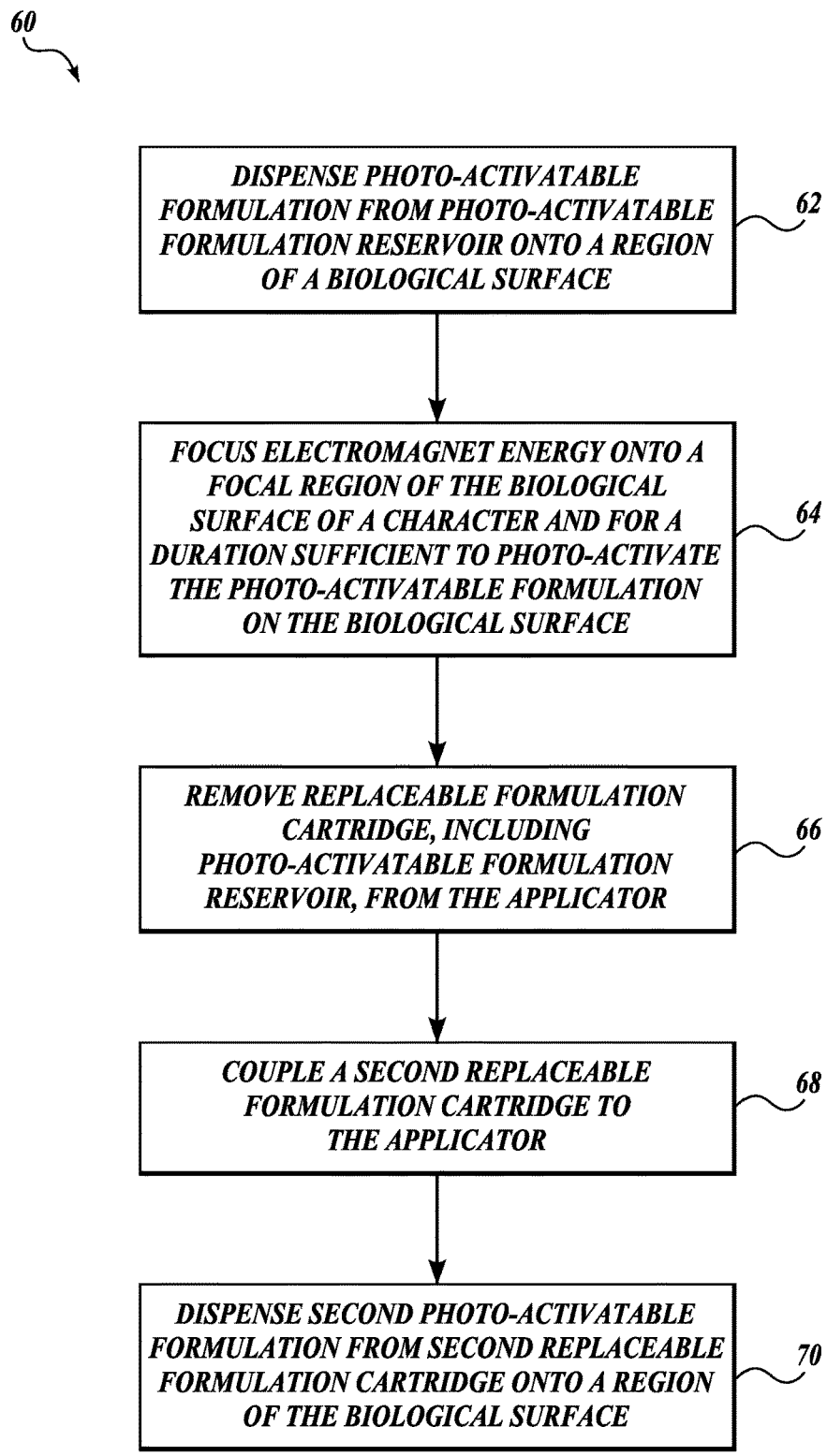
FIG. 9 depicts an embodiment of a method of applying a photo-activatable formulation, which can be performed using embodiments of applicators capable of dispensing and photo-activating photo-activatable formulations described herein.

FIG. 9 depicts an embodiment of a method 60 of applying a photo-activatable formulation, which can be performed using embodiments of applicators capable of dispensing and photo-activating photo-activatable formulations described herein. At block 62, photo-activatable formulation is dispensed by a dispenser portion of a photo-active formulation assembly from one or more photo-activatable formulation reservoirs onto one or more regions of a biological surface. At block 64, electromagnetic energy is focused by a photo-dose assembly operably coupled to the photo-active formulation assembly from at least one illuminator onto one or more focal regions of the biological surface. The focused electromagnetic energy is of a character and for a duration sufficient to photo-activate the photo-activatable formulation dispensed from the one or more photo-activatable formulation reservoirs. In one embodiment, the method 60 includes the steps depicted in blocks 62 and 64.

In an embodiment, the method 60 includes generating an electromagnetic energy stimulus responsive to one or more inputs indicative of a photo-curing composition type. For example, during operation the applicator 20 is operable to detect information about a formulation within a reservoir, cartridge, and the like, and to adjust one or more photo-curing parameters (e.g., a wavelength of the electromagnetic energy, an intensity of the electromagnetic energy, a duration of the electromagnetic energy, and the like) based on the detected information.

In an embodiment, the method 60 includes varying in real time one or more photo-curing parameters (e.g., a peak emission wavelength of the electromagnetic energy, an intensity of the electromagnetic energy, a duration of the electromagnetic energy, and the like) based on a detected measurement indicative of a curing rate.

In an embodiment, the method 60 includes varying one or more photo-curing parameters (e.g., a peak emission wavelength of the electromagnetic energy, an intensity of the electromagnetic energy, a duration of the electromagnetic energy, and the like) based on a detected measurement indicative of a photo-activatable formulation dispensing rate.

In an embodiment, the method 60 includes varying one or more photo-curing parameters (e.g., a peak emission wavelength of the electromagnetic energy, an intensity of the electromagnetic energy, a duration of the electromagnetic energy, and the like) based on a detected measurement indicative of which cartridge is dispensing photo-activatable formulation.

In an embodiment, the method 60 includes generating the focused electromagnetic energy responsive to one or more inputs indicative of a photo-curing protocol associated with a formulation within a reservoir, cartridge, and the like.

The method 60 optionally includes the steps depicted in blocks 66, 68, and 70. At block 66, the replaceable formulation cartridge is removed from an applicator that includes the photo-dose assembly. At block 68, a second replaceable formulation cartridge is coupled to the applicator. At block 70, a second photo-activatable formulation is dispensed from the second replaceable formulation cartridge onto the one or more regions of the biological surface. The steps depicted in blocks 66, 68, and 70 permit the applicator that includes the photo-dose assembly to be used with multiple replaceable formulation cartridges. In one example, this ability permits a user to dispense and photo-activate multiple photo-activatable formulations using the same applicator. As discussed above, in some embodiments, the applicator is configured to modify one or more spectral parameters of the electromagnetic energy from the photo-dose assembly based on the different replaceable formulation cartridges coupled to the applicator and/or the different photo-activatable formulations dispensed from the replaceable formulation cartridges.

Figure 10:
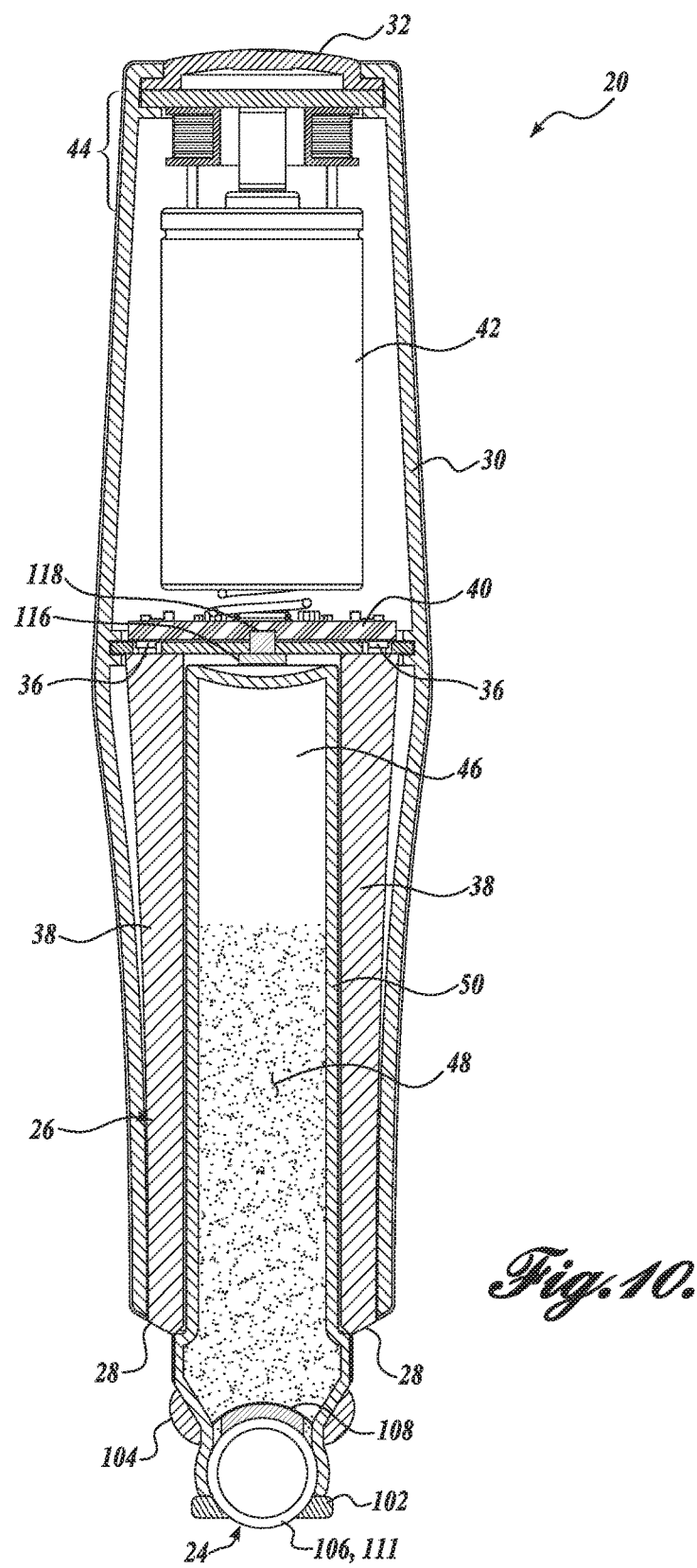
FIG. 10 depicts a side cross-sectional view of an applicator in accordance with embodiments described herein.

Referring to FIG. 10, additional elements will be discussed that may be added to any of the embodiments of the applicator 20. Although the elements of FIG. 10 are shown in combination with other elements, any one or more elements may be omitted, such that elements can be provided singly or in combination with one or more elements in embodiments of the applicator 20.

Referring to FIG. 10, in an embodiment, the applicator 20 includes a proximity sensor 102 that controls activation and deactivation of the illuminator 36 so that the illuminator 36 is activated when the dispenser portion 24 is within a certain distance to the user's skin, and the illuminator 36 is deactivated when the dispenser portion 24 is outside of the certain distance from the user's skin. The proximity sensor 102 can be placed on the inside or the outside of the applicator 20. In an embodiment, the proximity sensor 102 is placed on the outside of the applicator 20. The proximity sensor 102 may be an infrared sensor in order to detect when the dispenser portion 24 has moved a threshold amount away from the skin surface. Non-limiting examples of proximity sensors 102 include acoustic sensors (e.g., ultrasound sensors, acoustic transduces, and the like) conductance sensors, dielectric sensors (e.g., capacitance sensors), electrochemical sensors, fluorescence sensors, force sensors, heat sensors (e.g., thermocouples, thermistors, and the like), interdigital sensor, optical sensors, physiological sensors, proximity sensors (e.g., inductive proximity sensors, non-contact electronic proximity sensors, and the like), and the like.

In an embodiment, the proximity sensor 102 may be contact-based and will only permit the illuminator 36 to be active when the dispenser portion 24 is sensed to contact the skin surface. The contact may be sensed using any number of mechanisms known in the art. Non-limiting examples of this type of proximity sensor 102 include acoustic sensors (e.g., ultrasound sensors, acoustic transduces, and the like) conductance sensors, dielectric sensors (e.g., capacitance sensors), electrochemical sensors, fluorescence sensors, force sensors, and pressure sensors.

In another embodiment shown in FIG. 10, the dispenser portion 24 is a light transparent ball 24 and the illuminator 36 is configured to project images onto the skin surface of the user. In an embodiment, the images travel through the waveguides 38 from the illuminator 36 to the end of the applicator 20. The images may be used to display instructions for a treatment method using the applicator 20, to display a target or guide for where to direct the applicator for treatment, or to display notifications such as when the formulation needs to be replaced or the battery is running low on power. In an embodiment, an acquisition camera 104 may be disposed behind proximate to the dispenser portion 24 to take images of the user's skin. Such images may be used locally or transmitted to a remote device for diagnosing a condition of the user's skin. Such images are used to inform the targeting or guiding of the user to apply formulation to a particular area of the skin, either through the illuminator 36 or the external device display. In another embodiment shown in FIG. 10, the dispenser portion ball 24 may have a transparent or bio-compatible conductor coating 106. The transparent or bio-compatible conductor coating 106 encircles the entirety of the exterior of the dispenser portion ball 24. The transparent or bio-compatible conductor coating 106 is electrically connected to circuitry for performing any number of purposes. Suitable transparent, bio-compatible, conductive electrode materials for the ball dispenser portion 24 include, but are not limited to, polyethylenedioxythiophene (PEDOT) and nano-composites thereof (e.g., nano composites of PEDOT and grapheme). In an embodiment, the dispenser potion conductor coating 106 is coupled to a power supply and may be used to perform iontophoresis, wherein the dispenser portion 24 is operable as an electrode. Iontophoresis is a technique that uses a small electric current to deliver charged species across a membrane, in most cases an agent through the skin. By creating an electric field between at least two electrodes contacting the skin, active transport of an ion (charged molecule) through the skin can be achieved. The ion in an appropriate formulation is repelled by the source electrode that carries the same charge as the ion, driving it through the stratum corneum and towards the return electrode. Many active ingredients in skin care have ionic forms, so iontophoresis can improve penetration of these ingredients into the epidermis. A more complete description of a technique to use iontophoresis to deliver therapeutic agents to the user's skin is described in U.S. application Ser. No. 14/984, 104, which is incorporated herein by reference. In this case, the dispenser portion 24 itself acts as the repelling electrode. That is, the charge applied at the dispenser portion 24 is the same charge of the ionic species that is to be delivered.

In another embodiment shown in FIG. 10, the removable formulation cartridge 50 may be configured to have only a specific orientation in which it can be inserted into the applicator device in order to avoid mistakes in inserting the cartridge by the user. For example, referring to FIG. 10, the proximate end of the formulation cartridge 50 has a narrower diameter than the distal end (toward the dispenser portion 24), therefore, the formulation cartridge 50 can only be inserted into the applicator 20 when the proximate end is inserted first. In an embodiment, the cartridge 50 may have threads at one end only that thread onto the photo-does assembly. A plurality of different cartridges may be available in which each cartridge includes one of the specific formulations described above.

In another embodiment shown in FIG. 10, a shield 108 may be disposed behind the dispenser portion 24 which allows transmission of light from the illuminator 36 towards the dispenser portion 24, but blocks light from being reflected back towards the reservoir that stores the formulation 48. In an embodiment, this shield 108 may act like a one-way mirror and prevents reflected light from curing the formulation 48 inside the reservoir. In an embodiment, the shield 108 is a one way hemispherical mirror 108 provided behind the dispenser portion ball 24, wherein the hemispherical mirror 108 allows focusing of light from the illuminator 36 in one direction, but blocks light from returning to the interior of the cartridge 50.

In another embodiment of the applicator 20, different ranges of UV light wavelength may be used based on the formulation. Referring to FIG. 10, in an embodiment, the photo-active formulation assembly 22 includes an RFID or any other machine readable feature 116 encoded with information, such as the wavelength, time, amplitude, or a combination for activating the formulation 48, and the photo-dose assembly 26 includes an RFID reader or reader 118, such that when the photo-active formulation assembly 22 is inserted into photo-dose assembly 26, the reader 118 is in proximity to the machine readable feature 116 and can read the information provided on the machine readable feature 116. In an embodiment, based on the information obtained from the machine readable feature 116, the photo-dose assembly 26 controls the wavelength of the electromagnetic energy delivered by the illuminator 36, the time the illuminator 36 is on, the amplitude of the electromagnetic energy produced by the illuminator 36, or any combination. This way, the characteristics of the electromagnetic energy are automatically set into the applicator 20 to avoid any entry errors. In an embodiment, "machine readable feature" is used broadly to mean any type of storage device that has information which can be read electronically, such as RFID tags, magnetic chips, barcodes, 2-D barcodes, other electronically readable chips, marks, and the like.

In another embodiment shown in FIG. 10, the waveguide structures 38 may be placed outside of the cartridge 50. In an embodiment, the waveguide structures 38 are actually integrated with the cartridge 50 itself, but positioned on the outer surfaces of the cartridge 50, rather than through the middle of the applicator 20. For example, in an embodiment, the structural member 52 shown in FIG. 5 is eliminated and the waveguides 38 are fastened directly to the exterior surface of the cartridge 50 (the photo-active formulation assembly).

Figure 11:
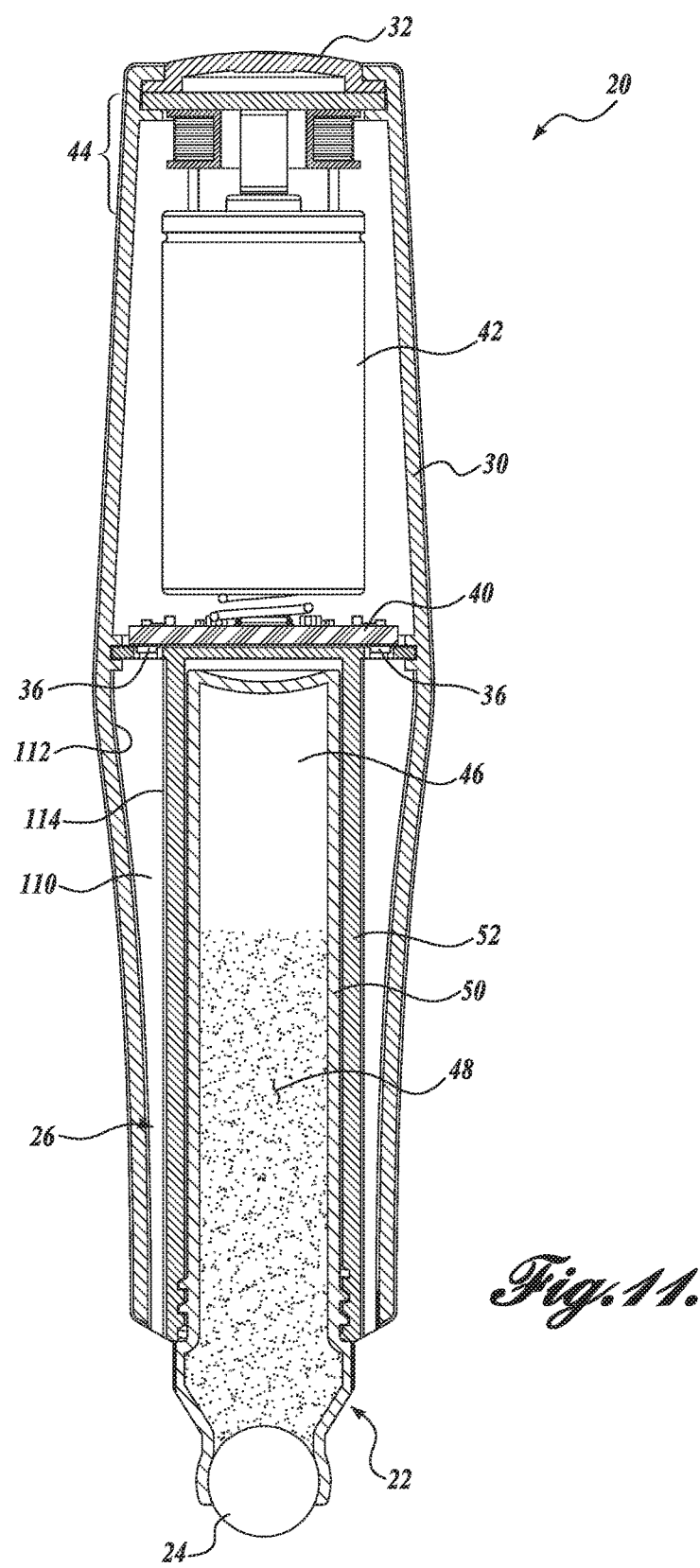
FIG. 11 depicts a side cross-sectional view of an applicator in accordance with embodiments described herein.

In another embodiment shown in FIG. 11, the applicator 20 is configured to allow free space propagation in a cavity 110 around the cartridge 50, whereby the light source illuminator 36 is located in the housing beyond the end of the inserted dispenser cartridge 50, with circumferential clearance around the cartridge 50 to allow light propagation from the illuminator 36 to the dispensing end of the cartridge 50. For instance, the cavity 110 may be configured as an elliptical reflector. In an embodiment, the cavity 110 is covered by a reflective surface 112 on the inside of the applicator 20 walls, and the cartridge 50 has a reflective surface 114 on the outside of the cartridge 50. Thus, forming the elliptical reflector.

In another embodiment shown in FIG. 10, the ball dispenser portion 24 has in place of the transparent or biocompatible conductor coating 106, a flexible outer surface 111 that encases a fluid or gel, such that the outer surface 111 can deform to adjust to the contours of the user's skin. In an embodiment, the outer surface 111 can be an elastomer, such as latex, rubber, polyisoprene, polybutadiene, chloroprene, butyl rubber, nitrile rubber, ethylene propylene rubber, or silicone. In an embodiment, the dispenser portion 24 contains a fluid or a gel within the flexible outer surface 111. In an embodiment, the dispenser portion ball 24 is slightly malleable and elastic, allowing it to conform to the skin while dispensing, but still be able maintain its shape within the bearing surface of the applicator 20.

It should be noted that for purposes of this disclosure, terminology such as "upper," "lower," "vertical," "horizontal," "inwardly," "outwardly," "inner," "outer," "front," "rear," etc., should be construed as descriptive and not limiting the scope of the claimed subject matter. Further, the use of "including," "comprising," or "having" and variations thereof herein is meant to encompass the items listed thereafter and equivalents thereof as well as additional items. Unless limited otherwise, the terms "connected," "coupled," and "mounted" and variations thereof herein are used broadly and encompass direct and indirect connections, couplings, and mountings.

The principles, representative embodiments, and modes of operation of the present disclosure have been described in the foregoing description. However, aspects of the present disclosure which are intended to be protected are not to be construed as limited to the particular embodiments disclosed. Further, the embodiments described herein are to be regarded as illustrative rather than restrictive. It will be appreciated that variations and changes may be made by others, and equivalents employed, without departing from the spirit of the present disclosure. Accordingly, it is expressly intended that all such variations, changes, and equivalents fall within the spirit and scope of the present disclosure, as claimed.

Further, the following patents and applications are incorporated herein expressly by reference for all purposes: U.S. application Ser. No. 14/613,059; U.S. application Ser. No. 14/612,215; U.S. application Ser. No. 11/346,622; U.S. application Ser. No. 11/116,434; U.S. Pat. Nos. 6,030,374; 7,004,933; 6,283,956; 7,494,503; U.S. application Ser. No. 09/819,082; U.S. application Ser. No. 09/819,083; U.S. Pat. Nos. 6,629,971; 7,201,765; U.S. application Ser. No. 11/212,916; U.S. application Ser. No. 11/332,517; U.S. Pat. Nos. 6,887,260; 6,936,044; U.S. application Ser. No. 11/366,811; U.S. application Ser. No. 09/322,981; U.S. application Ser. No. 09/759,094; U.S. Pat. Nos. 6,663,659; 6,676,655; U.S. application Ser. No. 10/665,390; U.S. application Ser. No. 10/903,483; U.S. application Ser. No. 11/187,241; U.S. application Ser. No. 11/205,316; U.S. application Ser. No. 60/601,995; U.S. application Ser. No. 11/272,042; U.S. application Ser. No. 60/627,110; U.S. application Ser. No. 60/626,492; U.S. application Ser. No. 12/583,562; U.S. application Ser. No. 12/583,578; U.S. application Ser. No. 12/550,749; U.S. application Ser. No. 12/550,799; U.S. application Ser. No. 12/550,464; and U.S. application Ser. No. 12/549,976.

The embodiments of the invention in which an exclusive property or privilege is claimed are defined as follows:

1. A method of applying a photo-activatable formulation comprising:

dispensing, by a dispenser portion of a photo-active formulation assembly, photo-activatable formulation from one or more photo-activatable formulation reservoirs onto one or more regions of a biological surface;

reading from a machine readable feature on the photo-active formulation assembly, information for activating the photo-activatable formulation; and focusing, by a photo-dose assembly operably coupled to the photo-active formulation assembly, electromagnetic energy from at least one illuminator onto one or more focal regions of the biological surface, wherein the wavelength of the electromagnetic energy, the time the illuminator is on, the amplitude of the electromagnetic energy, or any combination, is based on the information read from the machine readable feature.

\* \* \* \* \*